United States Patent [19]

Gristina

[11] 4,003,095
[45] Jan. 18, 1977

[54] TRISPHERICAL PROSTHETIC SHOULDER DEVICE

[75] Inventor: Anthony G. Gristina, Winston-Salem, N.C.

[73] Assignee: Howmedica, Inc., New York, N.Y.

[22] Filed: Apr. 29, 1976

[21] Appl. No.: 681,805

[52] U.S. Cl. .................... 3/1.91; 128/92 C
[51] Int. Cl.² ......................... A61F 1/24
[58] Field of Search .......... 3/1, 1.9–1.913; 128/92 C, 92 CA

[56] References Cited

UNITED STATES PATENTS

| 133,620 | 12/1872 | Benedict | 403/122 X |
|---|---|---|---|
| 3,638,243 | 2/1972 | Campbell, Jr. et al. | 3/1.91 |
| 3,694,820 | 10/1972 | Scales et al. | 3/1.91 |
| 3,815,157 | 6/1974 | Skorecki et al. | 3/1.91 |
| 3,842,442 | 10/1974 | Kolbel | 3/1.91 |
| 3,869,730 | 3/1975 | Skobel | 3/1 |
| 3,916,451 | 11/1975 | Buechel et al. | 3/1.91 |

FOREIGN PATENTS OR APPLICATIONS

| 426,096 | 6/1967 | Switzerland | 3/1.912 |
| 1,362,187 | 7/1974 | United Kingdom | 3/1.91 |

Primary Examiner—Ronald L. Frinks
Attorney, Agent, or Firm—Connolly and Hutz

[57] ABSTRACT

Biocompatible metal balls are secured by affixation stems to the humerus and the scapular region of the shoulder. The balls are rotatably captured between a pair of cutout plastic hemispheres, which are secured to each other to form a spheroid by a U-shaped collar. The prosthesis accordingly provides a wide range of articulation with substantially high stability.

10 Claims, 10 Drawing Figures

U.S. Patent  Jan. 18, 1977  4,003,095
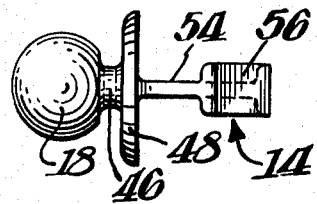
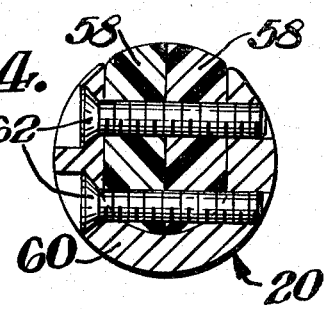
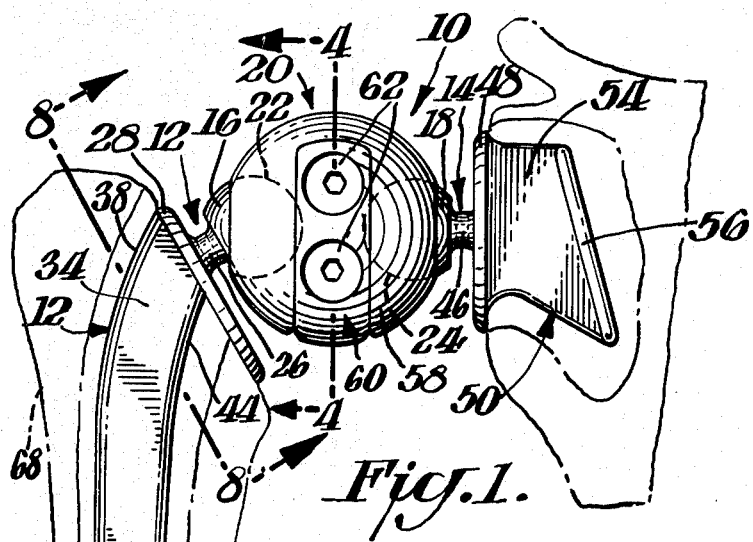
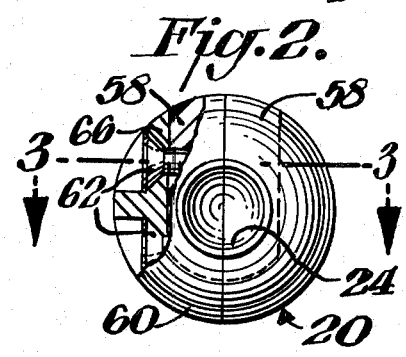
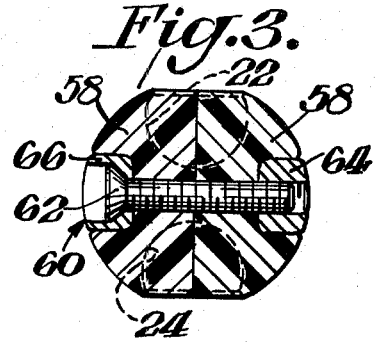
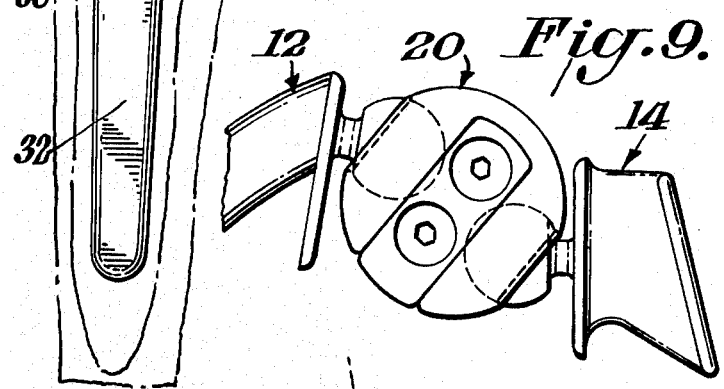
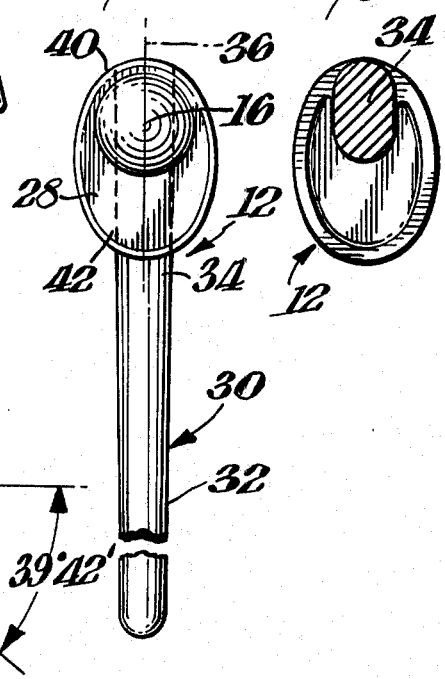
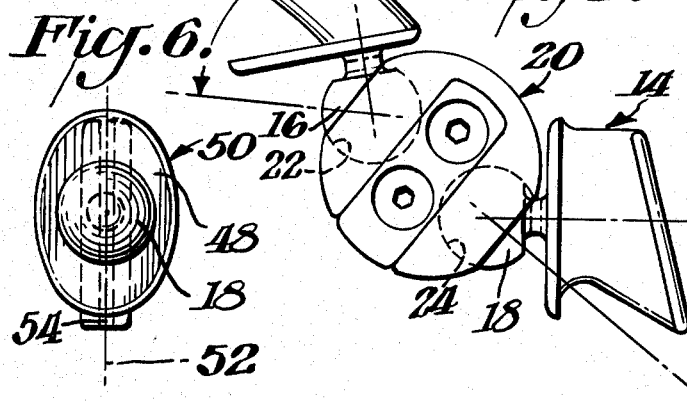

TRISPHERICAL PROSTHETIC SHOULDER DEVICE

CROSS REFERENCE TO RELATED APPLICATIONS

None.

BACKGROUND OF THE INVENTION

Total replacement of the humeral shoulder joint requires a prosthesis with stability and range of motion comparable to the human shoulder. Existing devices do not fully satisfy these requirements. An object of this invention is to provide a total replacement shoulder with a wide range of motion and stability for human requirements. Another object of this invention is to provide such a prosthesis which facilitates repair and replacement of wearing parts.

SUMMARY

In accordance with this invention, a ball-headed member of biocompatible metal is affixed to the top of the humerus by implanting its stem into the intermedullary canal of the humerus. The stem is disposed at an angle of approximately 30° to the axis of the ball and a flange separates the stem from the ball.

Another ball-headed member of biocompatible metal is attached to the scapular recess by, for example, a T-shaped stem. The balls are captured in spherical recesses disposed at about 180° from each other in a spheroidal component comprised of a pair of high-density cutout plastic hemispheres, which are joined together about the ball heads by a U-shaped collar inserted in the groove. The prosthesis provides a wide range of motion for the shoulder in which this prosthesis is implanted without sacrificing stability of the joint and in which wearing parts can be repaired or replaced with relative ease.

BRIEF DESCRIPTION OF THE DRAWING

Novel features and advantages of the present invention will become apparent to one skilled in the art from a reading of the following detailed description in conjunction with the accompanying drawings wherein similar reference characters refer to similar parts and in which:

FIG. 1 is a view in elevation showing an embodiment of this invention installed between the human shoulder and upper arm;

FIG. 2 is an end view partially broken away of the central spheroidal ball-capturing component of the embodiment shown in FIG. 1;

FIG. 3 is a cross-section view taken through FIG. 2 along the line 3—3;

FIG. 4 is a cross-sectional view taken through FIG. 1 along the line 4—4;

FIG. 5 is a top plan view of the ball-headed member shown in FIG. 1;

FIG. 6 is an end view of the scapular ball-headed member shown in FIGS. 1 and 5 viewed from the ball end;

FIG. 7 is a ball end view of the scapular component shown in FIG. 1;

FIG. 8 is a cross sectional view taken through FIG. 1 along the line 8—8;

FIG. 9 is a partial view of the prosthesis shown in FIG. 1 in an articulated position; and FIG. 10 is a partial view similar to FIG. 9 in a further articulated position.

DESCRIPTION OF THE PREFERRED EMBODIMENT

In FIG. 1 is shown trispherical prosthetic shoulder device 10 including a humeral component 12 and a scapular component 14 having respectively a humeral ball 16 of relatively small diameter, such as about ½ inch or 12.5 mm. and a scapular ball 18 of about the same diameter. Humeral ball 16 and scapular ball 18 are rotatably captured by a central spheroidal component 20 about 1 ⅛ inches or 28.5 mm. in diameter. Spherical sockets 22 and 24 in central component 20 rotatably capture slightly more than ½ of the spherical heads of balls 16 and 18 to securely rotatably capture them. Humeral component 12 also includes a neck 26 connecting ball 16 to flange 28 of substantially elliptical or oval shape (shown in FIG. 7). Ball 16 and neck 26 are eccentrically disposed approximately at one of the foci of elliptical flange 28. Stem 30 is connected to the other side of flange 28 and its slightly tapered end 32 is disposed at an angle of approximately 30° relative to flange 28. Neck 26 and ball 16 are disposed substantially perpendicularly to the other side of flange 28. The attached end 34 of stem 30 is slightly radially curved in planes parallel to the main axis 36 of flange 28, and has its convex surface 38 substantially contiguous to the outer edge 40 of the nearer end of flange 28. The other end 42 of flange 28 extends outwardly a considerable distance from the concave surface 44 of curved stem portion 34.

Humeral component 12 and scapular component 14 are made of a biocompatible metal, such as, for example Vitallium. Vitallium is the trademark of Howmedica, Inc., for a special cobalt-chromium alloy developed and used for cast partial and full dentures and for internal applications by surgeons. Cobalt and chromium constitute over 90% of its composition. Vitallium is characterized by a specific gravity of 8.29; tensile strength, 95,000 lb./sq.in.minimum; 2% offset yield strength, 65,000 lb./sq.in.minimum; reduction of area, 8% minimum; elongation, 8% minimum; and modulus of elasticity, 30,000,000 − 32,000,000 lb./sq.in. When polished, it is exceedingly smooth and permanently lustrous. Its outstanding qualities are clinical inertness in relation to living tissues and high degree of resistance to corrosion.

Scapular component 14 has a neck 46 joining ball 18 to substantially the center of elliptical flange 48, (as shown in FIG. 6), in a substantially perpendicular disposition. T-shaped affixation stem 50 is joined to the other side of flange 48 substantially in line with its major axis 52. Stem 50 includes a substantially narrow web 54 joining elongated base 56 to flange 48. Web 54 is longer at one end than the other and thus disposes base 56 at an acute angle relative to flange 48, such as approximately 15°. Scapular stem 50 and humeral stem 30 are both cemented in place by a suitable bone cement, such as methyl methacrylate.

Central component 20 includes a pair of plastic cutout hemispheres of biocompatible plastic 58, shown in FIGS. 2, 3, and 4 sharing spherical sockets 22 and 24 of a slightly greater than radial depth for capturing balls 16 and 18. Hemispheres 58 are, for example, made of high density or ultra-high density polyethylene. They are joined securely together about balls 16 and 18 by a U-shaped collar 60 and flat headed cap screws 62 threaded into arm 64 and passing through arm 66 of collar 60. Collar 60 and screws 62 are also made of Vitallium, for example. In the preferred embodiment the screw holes in plastic hemispheres 58 are slightly smaller than the major diameter of screws 62 in order to provide a "friction lock" feature.

FIGS. 1, 9 and 10 show various articulated positions of shoulder prosthesis 10. In FIG. 1, humeral component 12 and human arm 68 are disposed in a substantially downwardly extending vertical position with the inward motion of humeral component 12 arrested by contact of neck 26 on the lower edge of socket 22.

FIG. 9 shows a somewhat raised position of prosthesis 10 in which socket 24 of central component 20 has rotated upwardly about ball 18 until the outer edge of socket 24 is arrested on neck 26. This upward movement of socket 24 about ball 18 is approximately 40° upwards from the substantially horizontal position shown in FIG. 1. In FIG. 9 humeral component 12 is in the same relative position to central component 20 as shown in FIG. 1.

FIG. 10 shows humeral component 12 rotated upwardly to its extremity of travel in socket 22 until the other side of neck 26 strikes and is arrested on the edge of socket 22. This amount of movement of humeral component 12 from the position shown in FIG. 9 to that shown in FIG. 10 is approximately 75°. The total upward angular movement in the illustrated plane of movement of shoulder prosthesis 10 is, therefore, approximately 115°.

Prosthetic device 10, therefore, has the following features and advantages:

1. It exhibits an extensive range of motion without sacrifice of stability, and represents a stable interlocked joint with a wide range of articulation, in excess of articulated prostheses currently available.

2. The device provides a substitute for the humeral head and/or shaft and/or a portion of the glenoid. The humeral and scapular component are affixed with methyl methacrylate. Surgical procedure requires a Delto-Pectoral approach to shoulder joint with reflection of the capsule and insertion of the device. The capsule will be retained when indicated with the preservation of the musculo tendenous structures.

3. Equatorial overlap is controlled to provide extensive range of motion and stability of the tri-sphere interlock and at the same time controlling the dislocation forces below the force required to inflict failure at the cement/glenoid prosthesis interface.

4. Split plastic does not require a "popping type" assembly common to many current devices which results in localized deformation of plastic surfaces.

5. The self-locking feature of the screws provides inherent retention capability with plastic.

6. The undercut surface of the underside of the humeral flange provides for cement retention, which greatly enhances lateral stability and improves fixation.

7. The glenoid component incorporates a stem with a T-shaped section which resists imposed tensile loading thereby improving fixation of prosthesis.

8. The Split Collar provides for permanent securement of both components with articular media (plastic). It provides ease of assembly and disassembly; and allows for removal and replacement of plastic components without disturbance of affixed metal components.

9. Low frictional motion through approximately 300° spherical motion is obtainable.

10. Facile replacement of the ball-capturing high density polyethylene central spheroidal component is possible.

I claim:

1. A trispherical prosthetic shoulder device comprising a relatively small ball-headed humeral component of a biocompatible metal, a humeral stem on the ball-headed humeral component for affixing it to the intermedullary canal of the humerus, a humeral flange separating the ball-headed component from the stem, a ball-headed scapular component of a biocompatible metal, a scapular stem on the scapular component for attaching it to the scapular region of the shoulder, a scapular flange separating the scapular ball from the scapular stem, a spheroidal ball-capturing member having a pair of spherical sockets disposed substantially 180° from each other, the ball-capturing member comprising a pair of biocompatible cutout plastic hemispheres sharing the sockets between them, and clamping means joining the hemispheres together whereby the ball-heads are rotatably trapped in the sockets to provide a substantially stable shoulder prosthesis with a substantially wide range of movement.

2. A trispherical prosthetic shoulder device as set forth in claim 1 wherein the clamping means comprises a substantially U-shaped collar having a pair of arms and fastening means connecting the arms and extending through the hemispheres.

3. A trispherical prosthetic shoulder device as set forth in claim 1 wherein the humeral component has an elongated tapered stem for insertion into the intermedullary canal of the humerus.

4. A trispherical prosthetic shoulder device as set forth in claim 3 wherein the humeral stem is disposed approximately at an angle of 30° relative to the humeral flange, and the humeral ball-head is attached to the flange by a neck disposed approximately at an angle of 90° relative to the flange.

5. A trispherical prosthetic shoulder device as set forth in claim 4 wherein the portion of the humeral stem joining it to the humeral flange has a slight radial curve.

6. A trispherical prosthetic shoulder device as set forth in claim 1 wherein the scapular stem is substantially T-shaped.

7. A trispherical prosthetic shoulder device as set forth in claim 6 wherein the T-shaped stem has a flat base and the flat base is disposed at an acute angle relative to the scapular flange.

8. A trispherical prosthetic shoulder device as set forth in claim 1 wherein the flanges are substantially oval.

9. A trispherical prosthetic shoulder devices as set forth in claim 8 wherein the humeral ball is attached near one end of the oval humeral flange.

10. A trispherical prosthetic shoulder device as set forth in claim 1 wherein a short neck joins the ball-heads to the flanges.

* * * * *